United States Patent [19]

Fujita et al.

[11] 4,233,310
[45] Nov. 11, 1980

[54] ANTIARTERIOSCLEROTIC N-(MERCAPTOACYL)-HISTIDINES

[75] Inventors: Tadashi Fujita, Sakai; Masayuki Oya, Osaka; Toshio Watanabe, Suita; Takehisa Chiba, Kyoto, all of Japan

[73] Assignee: Santen Pharmaceutical Co., Ltd., Osaka, Japan

[21] Appl. No.: 771,839

[22] Filed: Feb. 24, 1977

[30] Foreign Application Priority Data

Mar. 16, 1976 [JP] Japan .................................. 51/28839

[51] Int. Cl.³ .................. A61K 31/415; C07D 233/64
[52] U.S. Cl. .................................. 424/273 R; 548/344
[58] Field of Search ...................... 548/344; 424/273; 260/534 S, 455 R

[56] References Cited

U.S. PATENT DOCUMENTS

| | | | |
|---|---|---|---|
| 2,090,756 | 8/1937 | Hansen et al. | 260/455 R |
| 2,396,879 | 3/1946 | Porter et al. | 260/455 R |
| 2,408,094 | 9/1946 | Pavlic | 260/455 R |
| 3,632,654 | 1/1972 | Van Auken et al. | 260/455 R |
| 3,988,471 | 10/1976 | Kohn et al. | 260/455 R |
| 3,991,077 | 11/1976 | Uzuki et al. | 548/344 |

OTHER PUBLICATIONS

Greenstein et al., Chemistry of the Amino Acids, vol. 2, pp. 965-969, N.Y., Wiley, 1961.
Photaki, The Role of Sulfur in Amino Acid Protective Group Chemistry In: Senning Topics in Sulfur Chemistry, p. 127, Stuttgart, Georg Thieme Publishers, 1976.
Reid, Organic Chemistry of Bivalent Sulfur, vol. 1, pp. 29-30, N. Y., Chemical Pub. Co., 1958.
Chemical Abstracts Subject Index, A-I, Jul.-Dec., 1962, vol. 57, p. 1209s, top of the middle column, (1963).
Wieland et al., Chem. Abst., 1953, vol. 47, Columns 2702-1.
Suguira, Y. et al., J. Am. Chem. Soc., 99, (5), 1581-1585, (1977).

Primary Examiner—John D. Randolph
Assistant Examiner—Richard A. Schwartz
Attorney, Agent, or Firm—Frishauf, Holtz, Goodman & Woodward

[57] ABSTRACT

This invention relates to the compound: N-(mercaptoacyl)-histidine represented by the following formula wherein n is 1 or 2, having activity as an antiarteriosclerosis agent, the intermediate thereof and a process for manufacture thereof.

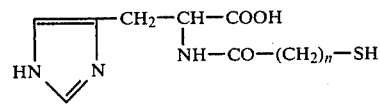

9 Claims, No Drawings

ANTIARTERIOSCLEROTIC N-(MERCAPTOACYL)-HISTIDINES

This invention relates to N-(mercaptoacyl)-histidine represented by the formula (I), a process for manufacture of the compound (I), N-(benzoylmercaptoacyl)-histidine represented by the formula (V) which is an intermediate of the compound (I), and an antiarteriosclerosis agent comprising the compound (I).

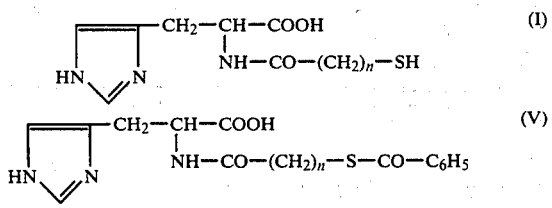

wherein n is 1 or 2.

Compound (I) and the intermediate thereof (V) have not been disclosed in any literature. Compound (I) has an action of improving and, as to be described hereinafter, has an action of decreasing lipid content in blood or liver and therefore it is useful as an antiarteriosclerosis agent. The intermediate (V) is important not only as an intermediate of compound (I) but also as a material which is expected to have a similar medical effect to that of compound (I). Compound (I) may be prepared by the following process.

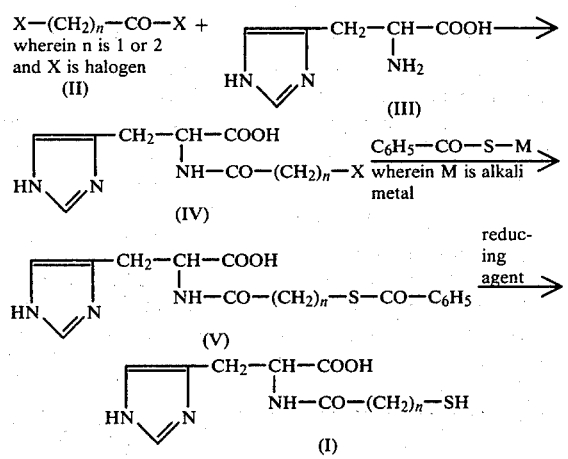

Halogenoacyl halide represented by the formula (II) reacts with histidine represented by the formula (III) by a known method such as Schotten-Baumann reaction to form N-(halogenoacyl)-histidine represented by the formula (IV). The resulting compound (IV) reacts with an alkali metal salt of thiobenzoic acid such as the sodium salt, potassium salt or aqueous solution thereof to form N-(benzoylmercaptoacyl)-histidine (V), the intermediate of compound (I). Compound (V) is contacted with a reducing agent such as aqueous ammonia to form N-(mercaptoacyl)-histidine which is the objective compound (I). As a solvent for these reactions, a lower alcohol such as methanol or ethanol may be used, but water is sufficient. The reation may be carried out at any temperature available, ranging from an elevated temperature to an ice-cooled temperature. The histidine (III) may be either the optically active form or the racemic form. If optically active material is used in the reaction, formulas (IV), (V) and (I) are obtained in optically active form.

The present invention is further illustrated by the following examples and by the pharmacological and toxicological studies in animals, but they are not be construed as limiting the present invention.

EXAMPLE 1

(1) Preparation of N-(benzoylmercaptoacetyl)-L-histidine (V, n=1)

155 g of L-histidine and 189 g of sodium hydrogen carbonate were dissolved in 1 liter of water and 124 g of chloroacetyl chloride was added dropwise to the resulting solution with stirring and ice-cooling. After allowing the reaction to proceed for 1 hour, an aqueous solution of sodium thiobenzoate which was prepared from 152 g of thiobenzoic acid and 220 ml of 5 N solution of sodium hydroxide solution, was added dropwise to the resulting solution and was kept standing overnight at room temperature to allow reaction. The resulting reaction solution was acidified with hydrochloric acid with ice-cooling to precipitate crystals. The crystals were collected on the filter and washed with water. The product thus obtained weighed 140 g (42 percent of the theoretical amount). Recrystallization from water gave colorless needles, m.p. 176°–177° C.

$[\alpha]_D^{24}$: −6.1° (c=1.0, water).

Anal. Calcd. for $C_{15}H_{15}N_3O_4S$: C, 54.05; H, 4.54; N, 12.60; Found: C, 54.18; H, 4.41; N, 12.70.

(2) Preparation of N-(mercaptoacetyl)-L-histidine (I, n=1)

10 g of N-(benzoylmercaptoacetyl)-L-histidine was added to 100 ml of aqueous ammonia and was stirred for 30 minutes at room temperature. The resulting solution was washed with ethyl acetate to remove benzamide, a by-product. The water resulting aqueous layer was concentrated under reduced pressure to give a crystalline residue. 50 ml of ethanol was added to the thus obtained crystalline residue ad precipitated crystals were collected by filtration and washed with ethanol. The product obtained weighed 4.8 g (70 percent of the theoretical amount). Recrystallization of dilute ethanol gave colorless prisms, m.p. 198°–200° C.

$[\alpha]_D^{24}$: +29.9° (c=1.0, water).

Anal. Calcd. for $C_8H_{11}N_3O_3S$: C, 41.91; H, 4.84; N, 18.33. Found: C, 42.01; H, 4.97; N, 18.25.

EXAMPLE 2

(1) Preparation of N-(3-benzoylmercaptopropionyl)-L-histidine (V, n=2)

155 g of L-histidine and 155 g of potassium carbonate were dissolved in 1 liter of water and 189 g of 3-bromopropionylchloride was added dropwise to the resulting solution with stirring and ice-cooling. After allowing the reaction to proceed for 1 hour, 183 g of potassium thiobenzoate was added to the resulting solution and was kept overnight at room temperature to allow reaction. The resulting reaction solution was acidified with hydrochloric acid with ice-cooling to precipitate crystals. The crystals were collected on the filter and washed with water. The product thus obtained weighed 153 g (44 percent of the theoretical amount). Recrystallization from water gave colorless needles, m.p. 170°–171° C.

$[\alpha]_D^{24}$: −7.0° (c=1.0, water).

Anal. Calcd. for $C_{16}H_{17}N_3O_4S$: C, 55.32; H, 4.93; N, 12.10. Found: C, 55.28; H, 4.96; N, 11.99.

(2) Preparation of N-(3-mercaptopropionyl)-L-histidine (I, n=2)

20 g of N-(3-benzoylmercaptopropionyl)-L-histidine was added to 200 ml of aqueous ammonia and this solution was treated in the same manner as those described in the Example 1-(2) N-(3-mercaptopropionyl)-L-histidine (I, n=2) was obtained in a yield of 11 g (78.1 percent of the theoretical amount). After recrystallization from dilute ethanol, the desired compound, melting at 219° C., was obtained.

$[\alpha]_D^{24}$: +14.1° (c=1.0, water)

Anal. Calcd. for $C_9H_{13}N_3O_3S$: C,44.43; H,5.38; N,17.27. Found: C, 44.22; H, 5.20; N, 17.02.

Pharmacological study (Hypolipid action)

A 2% aqueous solution of N-(mercaptoacetyl)-L-histidine and N-(3-mercaptopropionyl)-L-histidine, previously neutralized to pH 7.0 with sodium hydroxide, was administered orally to Wistar strain male rats at a dose of 100 mg/kg twice a day for one week. After the final administration of the test solution, the rats were fasted for 16 hours. Cholesterol, triglyceride and phospholipid levels in serum and liver were determined. The rats were divided into two groups. One group was fed a stock diet, and the other a 2% cholesterol-containing diet. The analytical results are shown in Tables 1 and 2.

TABLE 1

| | Group fed with stock diet | | |
|---|---|---|---|
| | Compound 1[1] | Compound 2[2] | Control[3] |
| (A) Serum lipid (mg/dl) | | | |
| Cholesterol content | 53.2 ± 1.9 | 45.4 ± 0.4 | 63.6 ± 2.2 |
| %[4] | 83.6 | 71.4 | 100 |
| Triglyceride content | 56.0 ± 5.6 | 49.5 ± 5.5 | 86.1 ± 6.8 |
| %[4] | 65.0 | 57.5 | 100 |
| Phospholipid Content | 95.1 ± 3.2 | 93.4 ± 4.8 | 113.3 ± 3.3 |
| %[4] | 83.9 | 82.4 | 100 |
| (B) Liver lipid (mg/total liver weight) | | | |
| Cholesterol content | 19.7 ± 0.8 | 18.9 ± 0.4 | 22.0 ± 0.8 |
| %[4] | 89.5 | 85.9 | 100 |
| Triglyceride content | 24.4 ± 2.0 | 30.8 ± 4.5 | 39.7 ± 1.5 |
| %[4] | 61.5 | 77.6 | 100 |
| Phospholipid content | 175.1 ± 7.3 | 163.6 ± 1.7 | 195.2 ± 7.3 |
| %[4] | 89.7 | 83.8 | 100 |

Results are expressed with mean value ± standard deviation
[1]:N-(mercaptoacetyl)-L-histidine
[2]:N-(3-mercaptopropionyl)-L-histidine
[3]:0.5ml of distilled water
[4]: $\frac{\text{Value in test compound administered rats}}{\text{Value in control administered rats}}$ (15) × 100 (%)

TABLE 2

| | Group fed with cholesterol containing diet | | |
|---|---|---|---|
| | Compound 1[1] | Compound 2[2] | Control[3] |
| (A) Serum lipid (mg/dl) | | | |
| Cholesterol content | 269.5 ± 4.8 | 246.9 ± 27.8 | 303.8 ± 14.9 |
| %[4] | 88.7 | 81.4 | 100 |
| Triglyceride content | '81.4 ± 10.2 | 79.2 ± 4.9 | 113.7 ± 13.3 |
| %[4] | 71.6 | 69.7 | 100 |
| Phospholipid content | 178.6 ± 9.8 | 173.9 ± 7.0 | 203.4 ± 9.9 |
| %[4] | 87.8 | 85.5 | 100 |
| (B) Liver lipid (mg/total liver weight) | | | |
| Cholesterol content | 52.4 ± 3.6 | 60.3 ± 4.0 | 62.8 ± 6.1 |
| %[4] | 83.4 | 96.0 | 100 |
| Triglyceride content | 17.0 ± 1.4 | 17.1 ± 1.5 | 17.4 ± 3.4 |
| %[4] | 97.7 | 98.3 | 100 |
| Phospholipid content | 112.6 ± 5.8 | 116.4 ± 4.2 | 120.8 ± 6.5 |
| %[4]/ | 93.2 96.4 | 100 | |

Results are expressed with mean value ± standard deviation
[1]:N-(mercaptoacetyl)-L-histidine
[2]:N-(3-mercaptopropionyl)-L-histidine
[3]:0.5ml of distilled water
[4] $\frac{\text{Value in a test compound administered rats}}{\text{Value in control administered rats}}$ × 100 (%)

TOXICOLOGICAL STUDY

Acute toxicity of N-(3-mercaptopropionyl)-L-histidine is shown in Table 3.

ANIMAL USED ddy Strain male rats, 4 weeks of age, weighing 18–20 g were placed in a room of constant temperature and humidity (24°±1° C., 55+5%) and fed freely a pellet diet (CE-2, made by Clea Japan Inc.) and water for one week. Out of them, rats showing normal growth were selected for the experiment.

METHOD OF ADMINISTRATION

N-(3-mercaptopropionyl)-L-histidine was added to physiological saline, and was neutralized to pH 7.0 with 4 N sodium hydroxide a 5% solution of this solution was used as the test solution, being administered intraperitoneally to the rats.

OBSERVATION

General symptoms and deaths were observed for 7 days after administration of the test solution, and the $LD_{50}$ value was determined from the number of deaths noted in 7-day period by the Litchfield-Wilcoxon method.

TABLE 3

| Test Compound | Acute toxicity ($LD_{50}$ by i.p.) |
|---|---|
| N-(3-mercaptopropionyl)-L-histidine | 4040mg/kg |

As clearly shown from the pharmacological and toxicological studies above, the compound of the present invention is useful as an antiarteriosclerosis agent. The adult dosage is within the range of 300–900 mg/day by oral administration.

For internal medicine, the compound may be supplied in the form of tablets, granules, powder or capsules. For this purpose, binding agents such as ethyl cellulose or polyvinyl pyrrolidone; forming agents such as lactose or crystalline cellulose; collapsing agents such as calcium carboxymethylcellulose; and lubricating agents such as talc or colloidal silica may be used.

The following are examples of formulations in which N-(3-mercaptopropionyl)-L-histidine is used as a model, but said compound may be substituted for other compounds of formula (I) in accordance with forms processed.

| (1) Tablet form | |
|---|---|
| N-(3-mercaptopropionyl)-L-histidine | 100mg |
| Ethyl cellulose | 50mg |
| Crystalline cellulose | 80mg |
| Calcium carboxymethylcellulose | 7mg |
| Magnesium stearate | 3mg |
| Total | 240mg |

Tablet may be coated with a film-coating or sugar-coating which is usually adopted.

| (2) Granular form | |
|---|---|
| N-(3-mercaptopropionyl)-L-histidine | 100mg |
| Polyvinyl pyrrolidone | 25mg |
| Lactose | 365mg |
| Talc | 10mg |
| Total | 500mg |
| (3) Powder form | |
| N-(3-mercaptopropionyl)-L-histidine | 100mg |
| Lactose | 500mg |
| Starch | 370mg |
| Colloidal silica | 30mg |
| Total | 1000mg |
| (4) Capsulated form | |
| N-(3-mercaptopropionyl)-L-histidine | 100mg |
| Lactose | 32mg |
| Crystalline cellulose | 56mg |
| Colloidal silica | 2mg |
| Total | 190mg |

What is claimed is:

1. N-(mercaptoacyl)-histidine represented by the formula

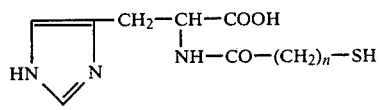

wherein n is an integer from 1 to 2.

2. N-(mercaptoacetyl)-histidine.
3. N-(3-mercaptopropionyl)-histidine.
4. N-(benzoylmercaptoacyl)-histidine represented by the formula (V) wherein n is 1 or 2

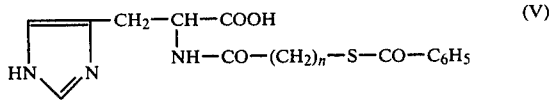

5. A compound of formula (V) of claim 4, wherein n is 1.
6. A compound of formula (V) of claim 4, wherein n is 2.
7. An antiarteriosclerosis composition containing an effective amount of N-(mercaptoacyl)-histidine represented by formula (I) wherein n is 1 or 2

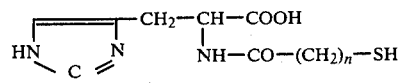

and a pharmacetical carrier.

8. A composition according to claim 7 wherein n is 1.
9. A composition according to claim 7 wherein n is 2.

* * * * *

UNITED STATES PATENT AND TRADEMARK OFFICE
CERTIFICATE OF CORRECTION

PATENT NO. : 4,233,310
DATED : November 11, 1980
INVENTOR(S) : FUJITA et al

It is certified that error appears in the above—identified patent and that said Letters Patent is hereby corrected as shown below:

Column 2, line 37: delete "water".

Column 3, line 4: delete "this" and insert --the resulting--.

Column 3, about line 54: Table 1, in note 4 appearing below the table, after "rats" delete "(15)".

Column 4, line 14: delete last line of Table 2 and replace with -- $\%^4$      93.2      96.4      100--.

Column 4, line 37: after "hydroxide" delete "a" and insert --. A--.

Column 6, line 27: (Claim 7) delete "formula (I)" and insert --the formula--.

Column 6, line 30: replace the formula with the following formula:

--  --.

Column 6, line 33: rewrite "pharmacetical" as --pharmaceutical--.

Signed and Sealed this

Sixth Day of July 1982

[SEAL]

Attest:

Attesting Officer

GERALD J. MOSSINGHOFF
*Commissioner of Patents and Trademarks*